United States Patent [19]

Hetzel et al.

[11] 4,079,068

[45] Mar. 14, 1978

[54] MANUFACTURE OF TETRAHYDROFURAN FROM THE DIACETATE OF 1,4-BUTANEDIOL

[75] Inventors: Eckhard Hetzel; Hans-Martin Weitz; Ludwig Vogel, all of Frankenthal; Juergen Hartig, Ludwigshafen, all of Germany

[73] Assignee: BASF Aktiengesellschaft, Ludwigshafen am Rhein, Germany

[21] Appl. No.: 606,487

[22] Filed: Aug. 21, 1975

[30] Foreign Application Priority Data

Sep. 7, 1974 Germany .................................. 2442886

[51] Int. Cl.$^2$ .......................................... C07D 307/08
[52] U.S. Cl. ................................................. 260/346,11
[58] Field of Search ................................... 260/346.1 R

[56] References Cited

U.S. PATENT DOCUMENTS 4,010,171  3/1977  Smith ........................... 260/346.1 R

FOREIGN PATENT DOCUMENTS 2,062,950  7/1971  Germany ...................... 260/346.1 R
1,170,222  11/1969  United Kingdom .......... 260/346.1 R

OTHER PUBLICATIONS

Walker et al., Principles of Chemical Engineering, New York-McGraw-Hill, (1927), pp. 564–569 and 574–577.
Kirk-Othmer, Encyclopedia of Chem. Technology, vol. 13, pp. 577 and 592–595, (1967), and vol. 7, pp. 204–214 and 243–244 (1965).

*Primary Examiner*—Henry R. Jiles
*Assistant Examiner*—Bernard Dentz
*Attorney, Agent, or Firm*—Keil, Thompson & Shurtleff

[57] ABSTRACT

Tetrahydrofuran is prepared from a compound containing butanediol or capable of generating butanediol. The butanediol-donating compound is an ester of butanediol which is reacted with hydrolysis and etherification by passing it downwardly through a distillation column together with an acid catalyst and passing steam upwardly therethrough. The product which distills off is tetrahydrofuran.

6 Claims, 1 Drawing Figure

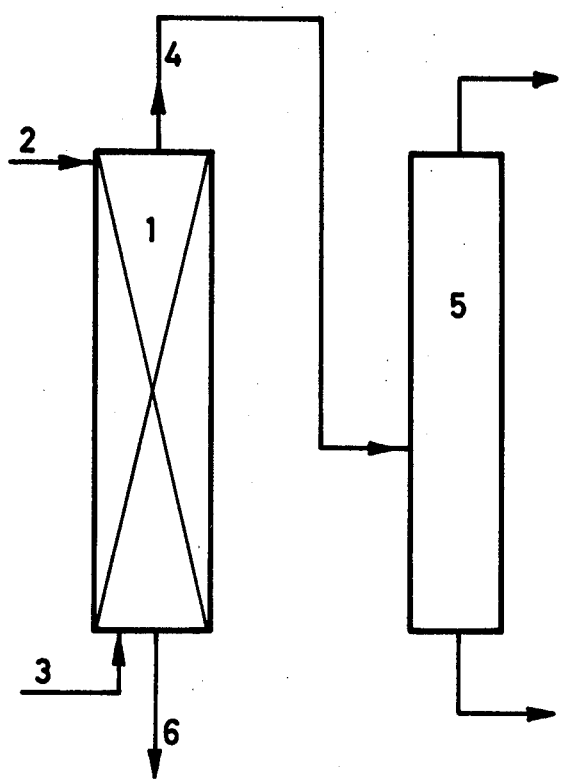

MANUFACTURE OF TETRAHYDROFURAN FROM THE DIACETATE OF 1,4-BUTANEDIOL

The present invention relates to a process for the manufacture of tetrahydrofuran (THF) from butanediol-1,4 esters in a reaction column.

The usual method of producing THF is by catalytic dehydration of butanediol-1,4 or by elimination of carbon monoxide from furfural followed by hydrogenation of the furan formed.

We have now found that THF may be produced at a fast rate and in excellent yield if an ester of butanediol-1,4 is reacted countercurrently with steam in the presence of an acid catalyst in a reaction chamber in the form of a distillation column.

The preferred ester of butanediol is butanediol-1,4 diacetate, which is readily available from butadiene via butenediol diacetate, which may be hydrogenated of butanediol-1,4 diacetate (see e.g. German Published Application 2,217,452).

The reaction proceeds according to the following equation:

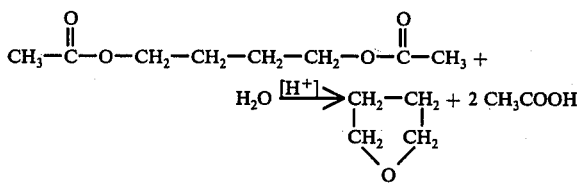

It is known that THF may be produced from butanediol-1,4 in the presence of acid catalysts by a steam distillation technique, but this requires a large excess of steam if the reaction is to proceed at a high rate.

If an attempt is made to carry out this reaction using butanediol diacetate in place of butanediol as starting material, the following difficulties occur. To complete the reaction within a satisfactory period, i.e. a period similar to that required by butanediol, it is necessary to use relatively large amounts of steam, since free acetic acid is produced as a further product of the reaction and this would react with the intermediate butanediol to reform the original compound.

It is therefore necessary to remove the acetic acid together with the THF formed and the excess steam from the reaction mixture. Since acetic acid has a boiling point which is 18° C above that of water, a specific amount of water is required for its complete removal depending on the vapor pressure of acetic acid at the reaction temperature. The necessarily large amount of steam required involves high energy costs.

The proposal has already been made to overcome the above difficulties by carrying out the reaction in two stages, i.e. in a reaction apparatus provided with a dephlegmator by means of which the THF and water are distilled over as an azeotropic mixture, whilst the acetic acid formed is removed in a second stage.

According to the invention, THF may be prepared from butanediol diacetate in shorter reaction times and with a low steam consumption by causing the reaction to take place in a reaction column in which the butanediol ester passes countercurrently to the rising steam. If, for example, referring to the accompanying drawing, an externally heated column (1) is used and a stream (2) of butanediol-1,4 diacetate and a sufficient amount of catalyst are passed to the top portion of the column, whilst steam (3) is introduced in the lower portion of the column, a mixture of THF, acetic acid and water is obtained at the top (4) of the column at 100% conversion and virtually 100% yield, which mixture may be readily separated (5). The catalyst may be withdrawn from the bottom of the column (6). The energy costs involved are very low and the process is particularly economical.

Advantageously, the amount of steam used is limited so that the excess thereof over the stoichiometric amount is not more than 20 moles, based on the amount of diacetate, although larger amounts may, of course, be used. The lower limit of the amount of water would be given, for stoichiometric reasons, by a molar ratio of diacetate to water of 1:1. However, since THF forms an azeotropic mixture with $H_2O$ (94.3% w/w of THF with 5.7% of $H_2O$), water is constantly removed with the THF during the reaction. Thus the lower limit is given by a ratio of 1:1.24. To achieve a satisfactory reaction rate, the amount of water should be greater and diacetate: water ratios of from 1:2 to 1:10 are advantageous.

The temperature at which the reaction is carried out is not particularly critical. In general, it is possible to use temperatures of from 80° to 200° C, the range of from 100° to 180° C and in particular of from 120° to 150° C neing preferred which means that superheated steam has to be used in this case. Below 80° C, the reaction rate drops considerably and above 200° C the starting product shows a tendency to decompose in the presnce of the catalyst. Atmospheric pressure is generally sufficient, but it is possible to carry out the process at somewhat reduced pressure or slightly elevated pressure, and the reaction may be carried out batchwise or continuously as desired. The temperature at which the reaction is carried out is conveniently controlled by the temperature of the steam, i.e. by using superheated steam.

The particularly preferred starting product is butanediol-1,4 diacetate. If desired, however, it is possible to use butanediol-1,4 monoacetate and butanediol-1,4, and mixtures of butanediol-1,4 diacetate produced after pre-hydrolysis of the diacetate.

The most suitable catalysts are mineral acids or strong organic and in particular non-volatile acids such as sulfuric acid, perchloric acid, hydrochloric acid, oxalic acid, benzenesulfonic acid and toluenesulfonic acid. The catalysts are preferably fed to the top of the column separately or together with the butanediol diacetate. However, low-boiling catalysts may be fed to the bottom of the column. A particularly suitable and the preferred catalyst is sulfuric acid. If desired, the catalyst may be recycled.

Commercially available inorganic or organic ion exchangers are suitable. They are easily removed from the reaction mixture and may be disposed in the reaction chamber in bulk form.

The catalyst concentration is not particularly critical. Although very low concentrations, for example, concentrations of less than 0.01% by weight, based on diacetate introduced, are effective, it is preferred to use concentrations of 0.1 to 20% and in particular of 0.5 to 10%, by weight. When using conventional acid ion exchangers, the amount is determined, according to the above figures, by calculating the stated acid concentration as sulfuric acid and using the corresponding acid equivalent of the ion exchanger.

Various forms of columns may be used as reaction chamber. Suitable columns are for example the plate columns containing sieve plates, valve plates or bubble-cap plates. In principle, use may also be made of packed columns. These have the disadvantage, however, of showing poor hold-up properties and must consequently be of a suitably large size to achieve adequate residence time. This should be noted when using acid ion exchangers which, of course, are usually employed in such packed columns.

The columns generally have a separating efficiency of from 5 to 150 theoretical plates, although larger columns are of no disadvantage industrially. This should permit a residence time of the butanediol ester of from 10 to 240 minutes and generally of at least 5 minutes.

EXAMPLE 1

The mixture of 360 g/hr (2.07 moles) of butanediol-1,4 diacetate and 7.2 g/hr of concentrated sulfuric acid is fed to the top plate of a heatable bubble-cap plate column (length 150 cm, 25 bubble-cap plates, diameter 55 mm, depth of liquid on each plate 12 mm) at a temperature of 130° C. 152 g/hr (8.45 moles) of water in the form of steam are fed to the bottom of the column, heated at about 160° C. Once the column has reached a state of equilibrium, 490 to 510 ml/hr of distillate are removed as overhead, this product containing 48% of acetic acid, 23.6% of water and 28.4% of THF. 10.5 g/hr of residue consisting of 7.2 g/hr of $H_2SO_4$, 2.8 g/hr of $H_2O$ and 0.5 g/hr of acetic acid are produced at the bottom of the column. The yield of THF is virtually quantitative (97.2%).

EXAMPLE 2

Using the apparatus described in Example 1, the reaction is repeated using a water/diacetate ratio of 2.73:1. The average residence time is 1 hour and the THF is obtained in 98% yield. The results of this test are largely as described in Example 1.

EXAMPLE 3

200 ml/hr of water in the form of superheated steam are fed to the bottom of a heated reaction tube (length 50 cm, diameter 24 mm), packed with an ion exchanger sold under the name of DOWEX 50 W (H+ form) at a temperature of 120° C whilst 0.40 ml/hr of butanediol-1,4 diacetate are passed through the top of the tube. The distillate removed as overhead is condensed and analyzed. It consists of 24.2% of water, 49.2% of acetic acid and 26.6% THF. The diacetate conversion is quantitative.

EXAMPLE 4

Using the apparatus described in Example 1, the reaction is carried out with a molar ratio of water to diacetate of 2:1, the feed to the top of the column being 180 g/hr of diacetate and 3.6 g/hr of sulfuric acid, the water being fed to the bottom of the column at a rate of 37.4 g/hr. Once the column has reached a state of equilibrium (the column is started without pre-filling), the distillate is removed as overhead at a rate of about 215 g/hr. This distillate consists of 8.6% of water, 57.1% of acetic acid and 34.2% of THF. The calculated yield is 98%.

EXAMPLE 5

Under the conditions described in Example 4, a mixture of 20% w/w of butanediol, 50% w/w of butanediol-1,4 monoacetate and 30% w/w of butanediol-1,4 diacetate is convertd to THF. The tetrahydrofuran is obtained in a yield of 97%. The course of the reaction is very much the same as that described in the above Examples.

We claim:

1. A process for the manufacture of tetrahydrofuran wherein the diacetate of butanediol-1,4 is reacted countercurrently with steam in the presence of an acid catalyst in a reaction chamber having the form of a distillation column in which the mol ratio of steam to said diacetate is maintained at 1.24 to 20 mols per mol of said diacetate and wherein tetrahydrofuran, acetic acid and water are withdrawn as overhead from said column, said distillation column being a plate column and said catalyst being a mineral acid or a strong organic acid the reaction temperature being 80°–200° C.

2. A process as claimed in claim 1, wherein superheated steam is used.

3. A process as claimed in claim 1, wherein the catalyst used is sulfuric acid.

4. A process for the manufacture of tetrahydrofuran which comprises feeding to the top portion of a plate distillation column butanediol-1,4-diacetate while feeding steam into the lower portion of said column and therein reacting at 80° to 200° C said steam and said diacetate in the presence of an acid catalyst, the molar ratio of diacetate to steam being fed to said column being maintained at a ratio of 1:2 to 1:10, respectively, and withdrawing as the overhead of said column tetrahydrofuran, acetic acid and water.

5. A process as claimed in claim 4 wherein the residence time in said column of said diacetate is 10 to 240 minutes.

6. A process for the manufacture of tetrahydrofuran, wherein the diacetate of butanediol-1,4 is reacted countercurrently with steam in the presence of an acid catalyst in a reaction chamber having the form of a distillation column in which the mol ratio of steam to said diacetate is maintained at 1.24 to 20 mols per mol of said diacetate and wherein the reaction chamber is a packed column, in which the catalyst is present in the form of a fixed bed and consists of an acid ion exchanger the reaction temperature being 80°–200° C.

* * * * *